(12) United States Patent
O'Connor et al.

(10) Patent No.: US 11,266,439 B2
(45) Date of Patent: *Mar. 8, 2022

(54) RETRACTION MECHANISM FOR MEDICAL DEVICE

(71) Applicant: Gyrus ACMI, Inc., Southborough, MA (US)

(72) Inventors: Michael O'Connor, Gurnee, IL (US); John Morici, Wauconda, IL (US); Michael DeRossi, Lindenhurst, IL (US); Steve Gaynes, Mchenry, IL (US)

(73) Assignee: Gyrus Acmi, Inc., Westborough, MA (US)

( * ) Notice: Subject to any disclaimer, the term of this patent is extended or adjusted under 35 U.S.C. 154(b) by 237 days.

This patent is subject to a terminal disclaimer.

(21) Appl. No.: 16/585,103

(22) Filed: Sep. 27, 2019

(65) Prior Publication Data

US 2020/0022725 A1 Jan. 23, 2020

Related U.S. Application Data

(63) Continuation of application No. 15/464,434, filed on Mar. 21, 2017, now Pat. No. 10,456,163.

(Continued)

(51) Int. Cl.
*A61B 17/34* (2006.01)
*H01F 7/02* (2006.01)
(Continued)

(52) U.S. Cl.
CPC ...... *A61B 17/3415* (2013.01); *A61B 17/3476* (2013.01); *H01F 7/0242* (2013.01);
(Continued)

(58) Field of Classification Search
CPC .............. A61B 5/1519; A61B 5/15113; A61B 5/15123; A61B 5/15194; A61B 5/150412;
(Continued)

(56) References Cited

U.S. PATENT DOCUMENTS 8,100,891 B2 1/2012 Baur
10,456,163 B2 * 10/2019 O'Connor .......... A61B 17/3415
(Continued)

FOREIGN PATENT DOCUMENTS

EP 2291130 B1 6/2015

OTHER PUBLICATIONS

"U.S. Appl. No. 15/464,434, Examiner interview Summary dated May 24, 2019", 3 pgs.
(Continued)

*Primary Examiner* — Mohamed G Gabr
(74) *Attorney, Agent, or Firm* — Schwegman Lundberg & Woessner, P.A.

(57) ABSTRACT

A device comprises a retractable shaft; a shaft biasing spring; and an actuator button. The retractable shaft is biased away from the actuator button by the shaft biasing spring. A magnetic attracting force is created between the retractable shaft and the actuator button upon actuation of the actuator button. Before actuation, a distance between the actuator button and the retractable shaft is great enough that the magnetic attracting force is less than a biasing force of the shaft biasing spring such that the retractable shaft is biased away from the actuator button. Upon actuation, the actuator button is depressed to make the distance between the actuator button and the retractable shaft sufficiently small such that the magnetic attracting force is greater than the biasing force of the shaft biasing spring to allow the retractable shaft to be biased towards the actuator button.

19 Claims, 5 Drawing Sheets

Related U.S. Application Data

(60) Provisional application No. 62/310,911, filed on Mar. 21, 2016.

(51) Int. Cl.
*A61B 17/00* (2006.01)
*A61B 17/32* (2006.01)
*A61B 17/3209* (2006.01)

(52) U.S. Cl.
CPC ..... *A61B 17/32093* (2013.01); *A61B 17/3496* (2013.01); *A61B 2017/00876* (2013.01); *A61B 2017/320028* (2013.01)

(58) Field of Classification Search
CPC .......... A61B 5/150503; A61B 5/15117; A61B 5/150152; A61B 5/150167; A61B 5/150175; A61B 5/150282; A61B 17/32002; A61B 17/32093; A61B 17/3401; A61B 2017/00876; A61B 2017/320028; B43K 7/12; H01F 7/0242; H01F 7/122
See application file for complete search history.

(56) References Cited

U.S. PATENT DOCUMENTS

| | | | |
|---|---|---|---|
| 2006/0056993 A1* | 3/2006 | Gombinsky | F15B 15/1476 417/321 |
| 2009/0175672 A1* | 7/2009 | Killion | B43K 23/001 401/100 |
| 2012/0057920 A1 | 3/2012 | Rolion | |
| 2017/0265883 A1 | 9/2017 | O'Connor et al. | |

OTHER PUBLICATIONS

"U.S. Appl. No. 15/464,434, Non Final Office Action dated Feb. 26, 2019", 10 pgs.

"U.S. Appl. No. 15/464,434, Notice of Allowance dated Jun. 26, 2019", 11 pgs.

"U.S. Appl. No. 15/464,434, Response filed Jan. 15, 2019 to Restriction Requirement dated Jan. 10, 2019", 2 pgs.

"U.S. Appl. No. 15/464,434, Response filed May 21, 2019 to Non Final Office Action dated Feb. 26, 2019", 12 pgs.

"U.S. Appl. No. 15/464,434, Restriction Requirement dated Jan. 10, 2019", 6 pgs.

O'connor, Michael, et al., "Retractable Shaft with Push-Button Mechanism", U.S. Appl. No. 62/310,911, (dated Mar. 21, 2016), 6 pgs.

* cited by examiner

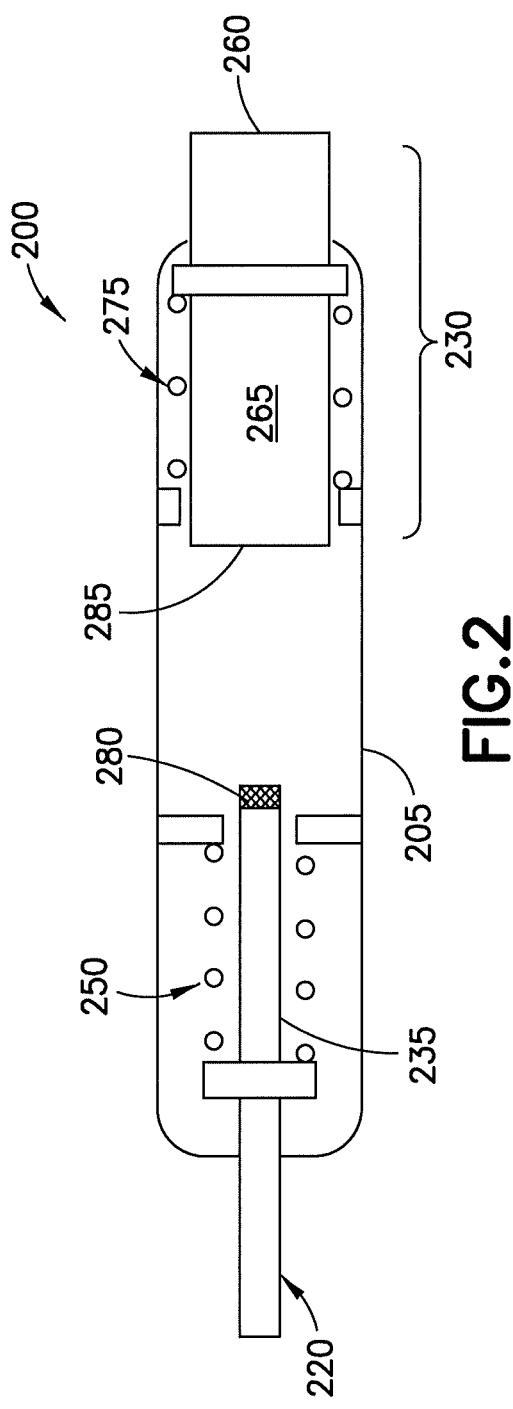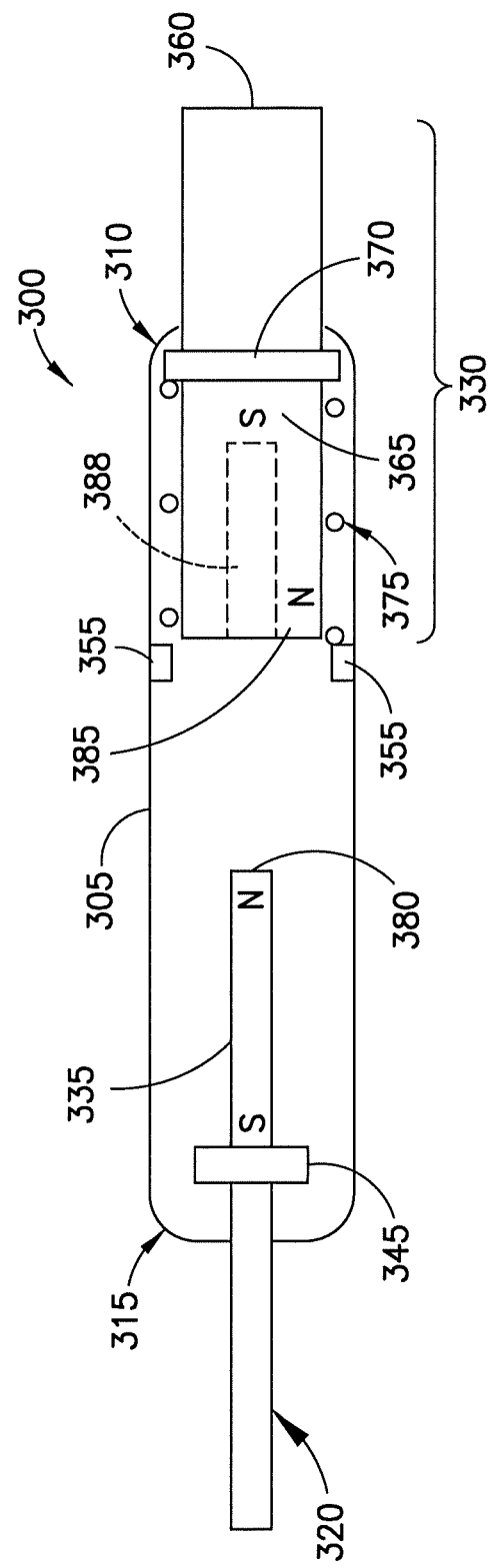

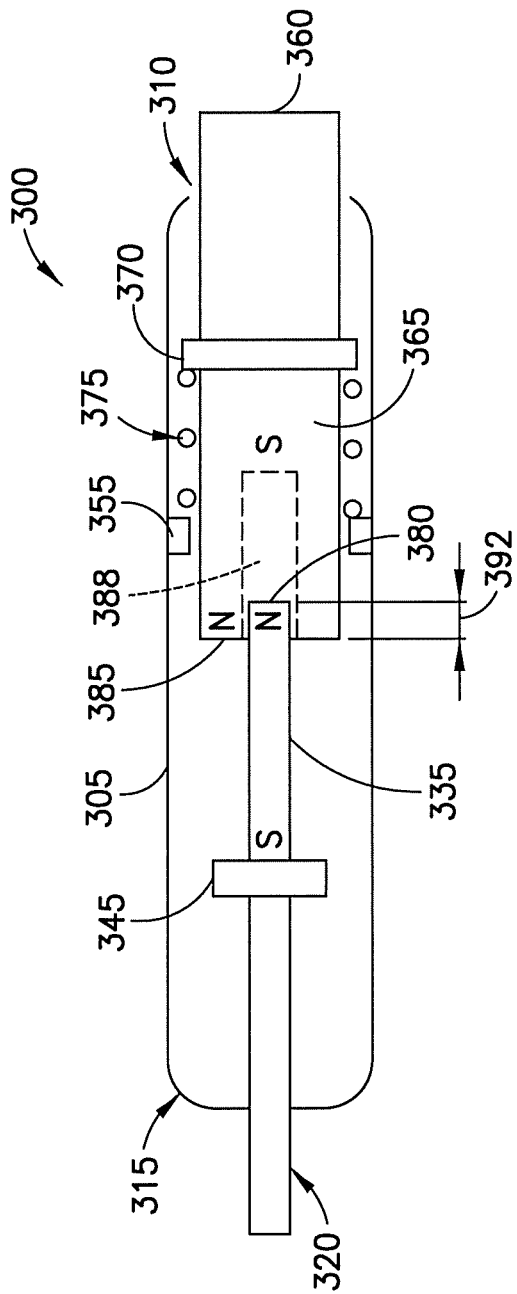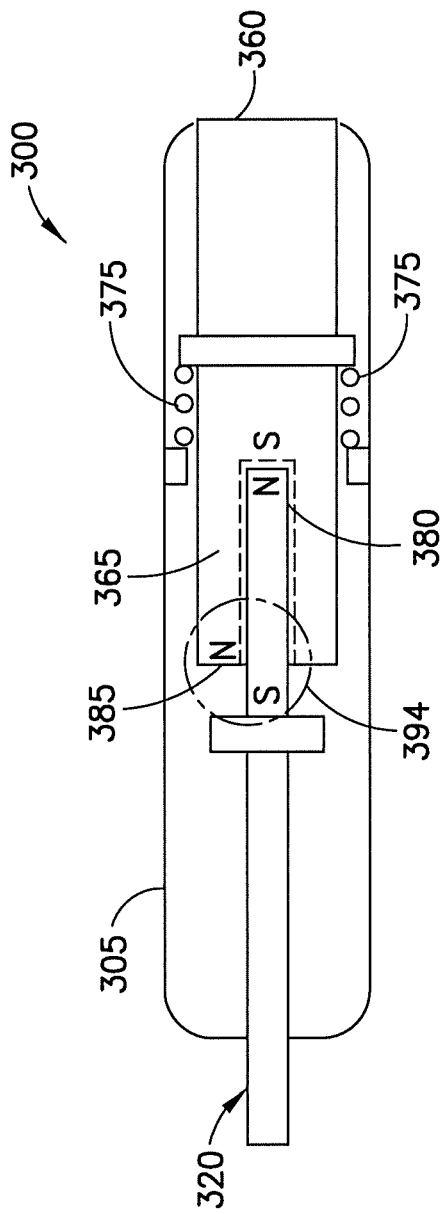

RETRACTION MECHANISM FOR MEDICAL DEVICE

CROSS REFERENCE

This patent application is a continuation of patent application U.S. Ser. No. 15/464,434, filed on Mar. 21, 2017, which claims priority to Provisional Patent Application U.S. 62/310,911, filed on Mar. 21, 2016, the disclosures of which are incorporated by reference herein in their entireties.

BACKGROUND

Field of the Invention

The exemplary and non-limiting embodiments described herein relate to devices having retraction mechanisms and, more specifically, to devices having retraction mechanisms based on the use of magnetics.

Brief Description of Prior Developments

U.S. Pat. No. 8,100,891 describes a medical appliance having a first setting device disposed at an outer side on a housing of the appliance and a second setting device disposed in the interior of the appliance, the first and second setting devices each comprising magnet elements that cooperate in such a way that one setting device actuates the other setting device for the transmission of adjustments. European Patent No. EP2291130 describes a cutting tool that includes an outer tubular member having a first magnet and an inner tubular member having a second magnet, the inner tubular member being slidably disposed within the outer tubular member such that an attractive force between the first magnet and the second magnet creates a preload force between the inner tubular member and the outer tubular member.

SUMMARY

In accordance with one aspect of the invention, a device comprises a retractable shaft; a shaft biasing spring; and an actuator button. The retractable shaft is biased away from the actuator button by the shaft biasing spring. A magnetic attracting force is created between the retractable shaft and the actuator button upon actuation of the actuator button. Before actuation, a distance between the actuator button and the retractable shaft is great enough that the magnetic attracting force is less than a biasing force of the shaft biasing spring such that the retractable shaft is biased away from the actuator button. Upon actuation, the actuator button is depressed to make the distance between the actuator button and the retractable shaft sufficiently small such that the magnetic attracting force is greater than the biasing force of the shaft biasing spring to allow the retractable shaft to be biased towards the actuator button.

In accordance with another aspect of the invention, a device comprises a retractable shaft and an actuator button. A first end of the retractable shaft includes a first magnet having a polarity and a first end of the actuator button includes a second magnet having the same polarity as the first magnet such that the first end of the retractable shaft is repelled from the first end of the actuator button. When the actuator button is pressed the first end of the actuator button travels past the first end of the retractable shaft such that the first magnet and the second magnet drive the retractable shaft towards the actuator button.

In accordance with another aspect of the invention, a method comprises providing a housing; providing a shaft having a medical tool located thereon, the shaft being slidably positioned in the housing and biased to extend from a distal end of the housing; providing an actuator button slidably positioned in the housing, the actuator button extending from a proximal end of the housing; and providing a magnetic attracting force between the shaft and the actuator button upon actuation of the actuator button. Before actuation, a distance between the actuator button and the shaft is great enough that the magnetic attracting force is less than a biasing force acting on the shaft such that the shaft is biased away from the actuator button. Upon actuation, the actuator button is depressed to make the distance between the actuator button and the shaft sufficiently small such that the magnetic attracting force is greater than the biasing force acting on the shaft to allow the shaft to be biased towards the actuator button.

In accordance with another aspect of the invention, a method comprises maneuvering a medical device to contact a tissue surface of a patient, the medical device having a shaft biased to extend from a distal end of a housing and further having an actuator button disposed at a proximal end of the housing, the shaft further having a medical tool associated therewith for contacting the tissue surface of the patient; and actuating the actuator button to retract the shaft into the housing.

BRIEF DESCRIPTION OF THE DRAWINGS

The foregoing aspects and other features of the invention are explained in the following description, taken in connection with the accompanying drawings, wherein:

FIG. 2 is a section view of another exemplary embodiment of a device having a tool retraction mechanism using a magnet and a ferromagnetic material;

FIG. 3A is a section view of another exemplary embodiment of a device having a tool retraction mechanism using similar polarities of two magnets;

FIGS. 3B-3D are section views of the device of FIG. 3A illustrating an operation of the device.

DETAILED DESCRIPTION

Figure 1A:
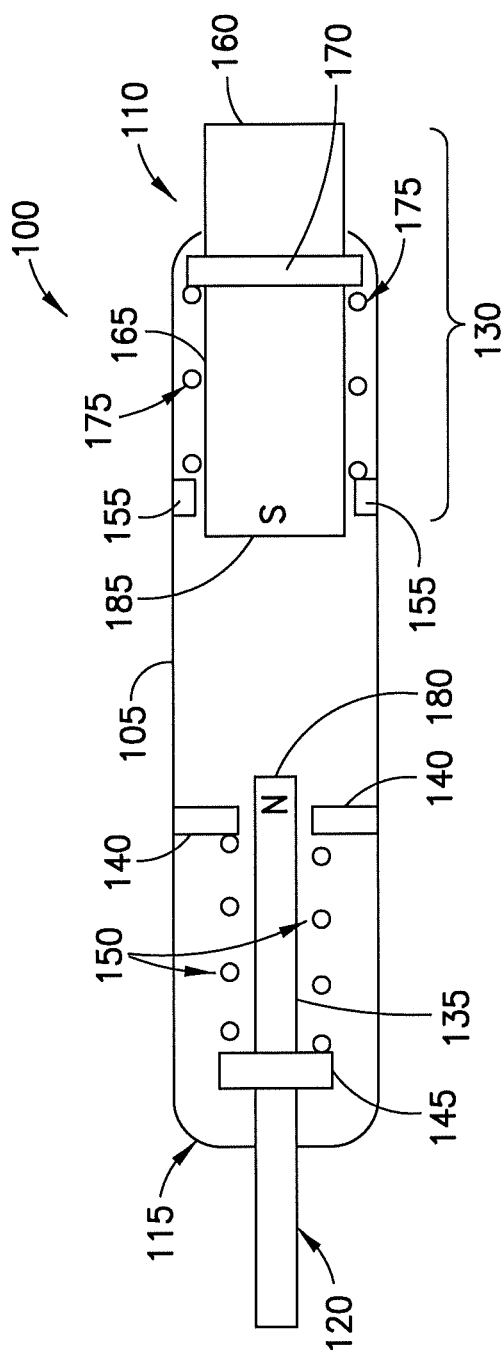
FIG. 1A is a section view of one exemplary embodiment of a device having a tool retraction mechanism using opposing polarities of two magnets.

Referring to FIG. 1A, one exemplary embodiment of a device is designated generally by the reference number 100 and is hereinafter referred to as "device 100." Although the features will be described with reference to the example embodiments shown in the drawings, it should be understood that features can be embodied in many alternate forms. In addition, any suitable size, shape, or type of elements or materials may be used.

Device 100 comprises a gripping portion or handle 105 having a proximal end 110 and a distal end 115. A tool 120 is slidably positioned in the handle 105 so as to extend from the distal end 115. An actuator in the form of a button mechanism 130 is slidably positioned in the handle 105 so as to extend from the proximal end 110. The tool 120 may be retractable into the handle 105 upon actuation of the button mechanism 130. The device 100 is not limited to the actuator being the button mechanism 130, however, as the actuator may be a sliding mechanism protruding from a side of the handle 105.

The tool 120 may comprise a shaft 135, which may be slidable in the distal end 115 partially through a front opening in the handle 105 and partially through a forward shoulder 140. The tool 120 may further comprise a shaft collar 145 or O-ring located on a portion of the shaft 135 within the handle 105 to retain the tool 120 in the front opening at the distal end 115 of the handle 105. The tool 120 may further comprise a biasing spring 150 (e.g., a coil spring) positioned around the shaft 135 and aft of the shaft collar 145 and forward of the forward shoulder 140. The biasing spring 150 may bias the tool 120 in the distal direction through the front opening and may hold the tool 120 in a stationary position relative to the handle 105. The shaft 135 may substantially be a rod or a tube and may form all or a portion of a tool for a medical device, such as a needle, a knife, a blade, a cannula, a trocar, or the like.

The button mechanism 130 may be slidable in the proximal end 110 of the handle 105 partially through a rear opening and partially through a rear shoulder 155. The button mechanism 130 may comprise a control surface 160 and a plunger 165, which may be integral with or attached to the control surface 160. The button mechanism 130 may further comprise a button collar 170 or O-ring located on a portion of the plunger 165 within the handle 105 to retain the plunger 165 in the rear opening at the proximal end 110 of the handle 105. The button mechanism 130 may further comprise a button return spring 175 (e.g., a coil spring) positioned around the plunger 165 and aft of the rear shoulder 155 and forward of the button collar 170. The button return spring 175 may bias the plunger 165 in the proximal direction through the rear opening and may hold the control surface 160 in a stationary position relative to the handle 105.

The biasing spring 150 and the button return spring 175 may each bias the tool 120 and the button mechanism 130, respectively, in opposing directions.

A proximal end of the shaft 135 may include or be configured as a shaft magnet 180, and a distal end of the plunger 165 may include or be configured as a button magnet 185. The shaft magnet 180 and the button magnet 185 define a magnetic mechanism that creates an attractive force between the proximal end of the shaft 135 and the distal end of the plunger 165. To create the attractive force, the shaft magnet 180 and the button magnet 185 may be arranged as magnetic poles having opposite polarities (e.g., one magnet is a north pole, and the other magnet is a south pole).

Figure 1B:
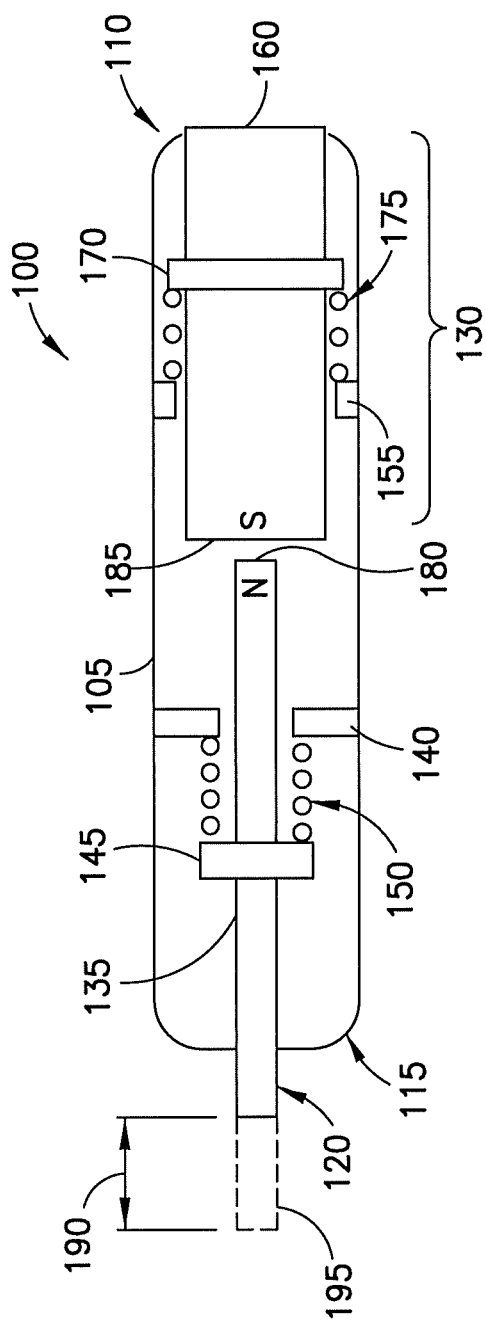
FIG. 1B is a section view of the device of FIG. 1A illustrating one exemplary operation of the device.

Referring to FIG. 1B, the operation of device 100 is shown. When the control surface 160 of the button mechanism 130 is actuated by pushing in the forward direction (the "button" is pressed), the button return spring 175 may be compressed and the distal end of the plunger 165 moved into close proximity with the proximal end of the shaft 135. Because the shaft magnet 180 and the button magnet 185 are of opposing polarities, the shaft magnet 180 and the button magnet 185 attract each other. The biasing spring 150 is configured to have a force that may be overcome by the attraction of the shaft magnet 180 and the button magnet 185. In overcoming the force of the biasing spring 150, the shaft 135 is caused to move in the proximal direction and retract the distal end of the tool 120. The lengths of the shaft 135 and the plunger 165 and their positioning in the handle 105 are configured to, in conjunction with suitable actuation of the button mechanism 130, retract the tool 120 a desired distance 190 relative to a pre-retracted position 195. In one exemplary embodiment, when the button mechanism 130 is actuated, the shaft magnet 180 may be attracted to the button magnet 180 as long as the "button" is depressed. When the "button" is released, the biasing forces of the biasing spring 150 and the button return spring 175 may overcome the magnetic attraction, and the biasing spring 150 and the button return spring 175 extend. In another exemplary embodiment, the button mechanism 130 may be a one-time use mechanism that retracts the shaft 135 to the proximal position, the magnetic attraction being greater than the biasing force of either of the biasing spring 150 and the button return spring 175. In such a configuration, the shaft 135 and the plunger 165 may remain in the attracted configuration.

Referring now to FIG. 2, another exemplary embodiment of a device is designated generally by the reference number 200 and is hereinafter referred to as "device 200." Device 200 may be similar in some exemplary aspects to device 100 and may have a handle 205, a tool 220 with a shaft 235, and a button mechanism 230 with a plunger 265 and a button return spring 275, but in device 200 one of a rearward portion of the shaft 235 and a forward portion of the plunger 265 includes a magnet 280, and the other of the rearward portion of the shaft 235 and the forward portion of the plunger 265 includes a ferromagnetic material 285. As shown, the shaft 235 includes the magnet 280 and the plunger 265 includes the ferromagnetic material 285. However, the device 200 is not limited in this regard, and the shaft 235 may include the ferromagnetic material 285 and the plunger 265 may include the magnet 280. When a control surface 260 is actuated by pushing in the forward direction (the "button" is pressed), the plunger 265 is moved in the distal direction, and the magnet 280 is attracted to the ferromagnetic material 285, thereby drawing the shaft 235 in the proximal direction for retraction.

In either the configuration of the device 100 of FIG. 1A or the configuration of the device 200 of FIG. 2, in an initial state (before pressing the button), the distance between the proximal end of the shaft 135, 235 and the distal end of the plunger 165, 265 is sufficiently great such that a magnetic attraction force may be overcome by the biasing forces of the biasing spring 150, 250 and the button return spring 175, 275, so that the button mechanism 130, 230 is biased proximally relative to the handle 105, 205 and the shaft 135, 235 is biased distally relative to the handle 105, 205.

In either of the foregoing exemplary embodiments, either the biasing spring 150, 250 or the button return spring 175, 275 is optional.

Also, in either of the foregoing exemplary embodiments when the biasing spring 150, 250 and/or the button return spring 175, 275 are used, the control surface 160, 260 may be released and the button return spring 175, 275 may drive the button mechanism 130, 230 in the proximal direction. In doing so, the tool 120, 220 may be further retracted. In another exemplary embodiment, if the biasing spring 150 is stronger than the button return spring 175 but the magnetic attraction between the two is not overcome by the springs, then the shaft 135 and the button magnet 185 may remain locked together magnetically, and both would be driven to a more distal position. Doing so would render the button mechanism 130 to a more distal position, which may be practical for a one-time use device.

Referring now to FIG. 3A, a device 300 comprises a gripping portion or handle 305 having a proximal end 310 and a distal end 315. A tool 320, which may be similar in some exemplary aspects to the tool of device 100, is slidably positioned in the handle 305 so as to extend from the distal end 315. An actuator in the form of a button mechanism 330 is slidably positioned in the handle 305 so as to extend from the proximal end 310. The tool 320 may be retractable into the handle 305 upon actuation of the button mechanism 330.

The tool 320 may comprise a shaft 335, which may be slidable in the distal end 315 of the handle 305 partially through a front opening. The tool 320 may further comprise a shaft collar 345 or O-ring located on a portion of the shaft 335 within the handle 305 to retain the tool 320 in the distal end 315 of the handle 305. Optionally, a biasing spring (e.g., a coil spring) may be positioned around the shaft 335 and aft of the shaft collar 345 and forward of a forward shoulder. Such a biasing spring, if present, may bias the tool 320 in the distal direction through the front opening, similar to the shaft 135 of the tool 120 of the device 100. With regard to the tool 320, the shaft 335 may substantially be a rod or a tube and may form all or a portion of a tool for a medical device, such as a needle, a knife, a blade, a cannula, a trocar, or the like.

The button mechanism 330 may be slidable in the proximal end 310 of the handle 305 partially through a rear opening and partially through a rear shoulder 355. The button mechanism 330 may comprise a control surface 360 and a plunger 365, which may be attached to or integral with the control surface 360. The button mechanism 330 may further comprise a button collar 370 or O-ring located on a portion of the plunger 365 within the handle 305 to retain the plunger 365 in the proximal end 310 of the handle 305. A cavity 388 may be formed in a forward end of the plunger 365 for receiving the shaft 335 during operation of the device 300. Optionally, the button mechanism 330 may further comprise a button return spring 375 (e.g., a coil spring) positioned around the plunger 365 and aft of the rear shoulder 355 and forward of the button collar 370. Such a button return spring 375, if present, may bias the plunger 365 in the proximal direction through the rear opening and hold the control surface 360 in a stationary position relative to the handle 305.

The shaft 335 may be configured as a shaft magnet 380 (or it may include the shaft magnet 380 at a proximal end of the shaft 335) such that a proximal end of the shaft 335 has a magnetic polarity. The plunger 365 may also be configured as a plunger magnet 385 (or it may include the plunger magnet 385 at a distal end of the plunger 365) such that a distal end of the plunger 365 proximate a mouth of the cavity 388 has the same polarity as the proximal end of the shaft 335. A bottom of the cavity 388 or an area proximate the bottom of the cavity 388, however, has the opposite polarity as at the mouth of the cavity 388. The shaft magnet 380 and the plunger magnet 385 define a magnetic mechanism or magnetic means that creates a repulsive force between the proximal end of the shaft 335 and the distal end of the plunger 365. The repulsive force is created by the shaft magnet 380 and the plunger magnet 385 arranged as magnetic poles having the same polarities (both magnets are north poles or both magnets are south poles). As shown, both the shaft magnet 380 and the plunger magnet 385 are north poles, with a more distal portion of the shaft 335 being a south pole and a more proximal portion of the plunger 365 also being a south pole. The present device 300 is not so limited, however, as both of these polarities may be reversed. In any configuration, in an initial state, the shaft magnet 380 and the plunger magnet 385 repel each other and are driven away from each other, without need of a biasing spring.

Referring now to FIG. 3B, the plunger magnet 385 at the distal end of the plunger 365 has the cavity 388 in which the proximal end of the shaft magnet 380 may be received. Thus, as the control surface 360 is actuated by pushing in the forward direction (the "button" is pressed), the plunger magnet 385 at the mouth of the cavity 388 may move over the shaft magnet 380 on the proximal end of the shaft 335. As the plunger magnet 385 and the shaft magnet 380 pass each other as indicated by arrow 392, the repulsive force drives the shaft 335 (and the tool 320) in the proximal direction, thereby retracting the tool 320. In one exemplary embodiment, the distal end of the plunger 365 may be configured simply as a cylinder of non-ferromagnetic material having the cavity for receiving the shaft 335, with the plunger magnet 385 configured as a donut-shaped member over the distal end of the plunger 365. In another exemplary embodiment, the shaft magnet 380 and the plunger magnet 385 may be coaxially arranged.

Referring now to FIG. 3C, upon additional pressing of the control surface 360, the "button" is pressed farther into the handle 305, and the plunger magnet 385 is moved farther past the shaft magnet 380. In doing so, the repulsive force between the shaft magnet 380 on the proximal end of the shaft 335 and the plunger magnet 385 on the distal end of the plunger 365 becomes weaker, but an attractive force 394 may be generated between the plunger magnet 385 on the distal end of the plunger 365 and the more distal portion of the shaft 335. This attractive force 394 may cause the retraction of the tool 320

Figure 3D:
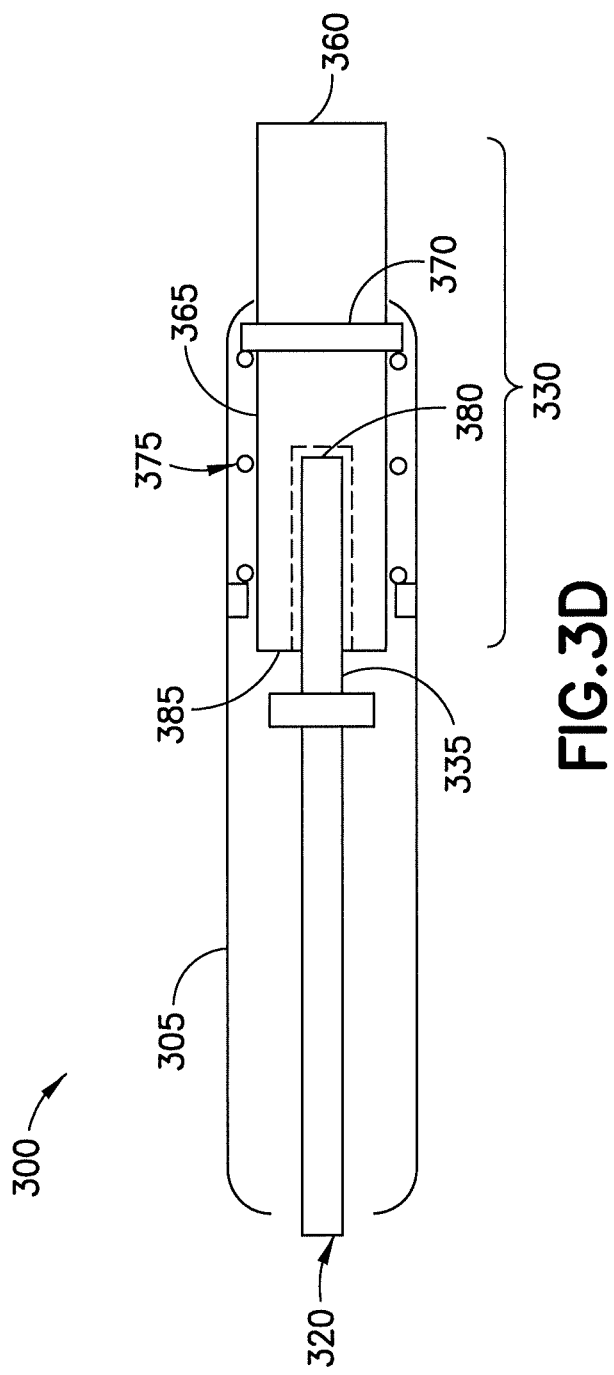

Referring now to FIG. 3D, in an embodiment in which the optional button return spring 375 is incorporated into the button mechanism 330, releasing the control surface 360 may return the button mechanism 330 to a pre-pressed state, thereby retracting the tool 320 completely (or substantially completely) into the handle 305.

Any of the mechanisms of the above-described embodiments may be applicable to devices such as trocars, needles, blades, and the like.

Figure 4:
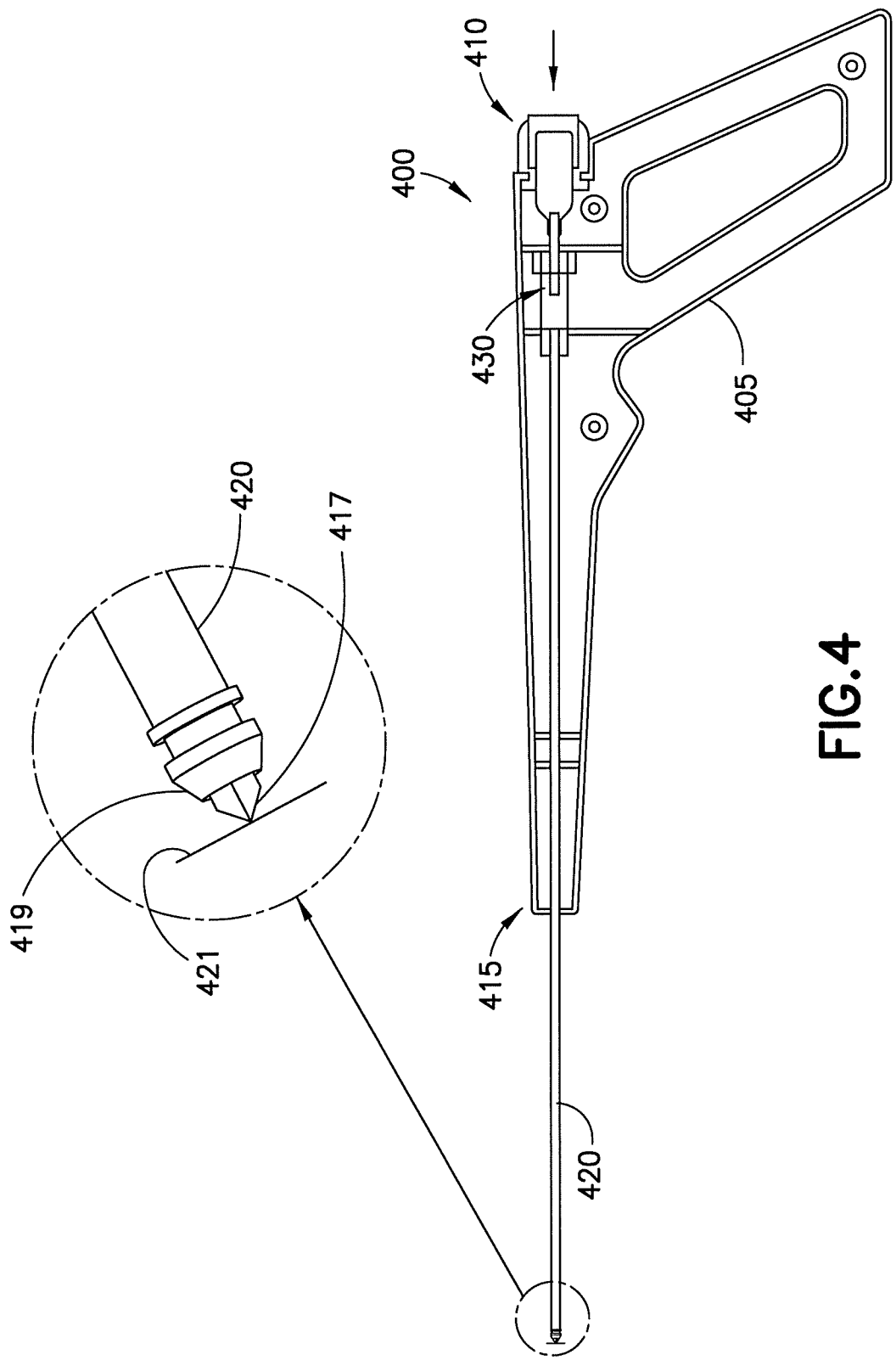
FIG. 4 is a side view with inset of another exemplary embodiment of a device having a tool retraction mechanism, the device being usable in a surgical procedure.

Referring now to FIG. 4, another exemplary embodiment of a device is designated generally by the reference number 400 and is hereinafter referred to as "device 400." Device 400 is a medical device and comprises a handle 405 having a proximal end 410 and a distal end 415, with a tool 420 located in the distal end 415. A button mechanism 430 is located in the proximal end 410 and is operably coupled to the tool 420 using a magnetic mechanism as in the exemplary embodiments described herein so as to cause the retraction of the tool 420 when the button mechanism 430 is actuated. The tool 420 may comprise a sharpened cannula or knife 417 around which a removable vent tube 419 is positioned.

In one exemplary operation of the device 400, a user may maneuver the device 400 so as to insert the knife 417 through an epidermis or other layer of tissue 421 of a patient to make an opening. As the knife 417 is inserted farther, an outer surface of the vent tube 419 (which may be angled as shown) spreads the epidermis or tissue to define the opening of a desired size. Once the vent tube 419 is in place in the opening, the button mechanism 430 is actuated, and the knife 417 is retracted from the opening and the vent tube 419. The device 400 may then be separated from the vent tube 419, leaving the vent tube 419 in the opening in the patient.

In one example, a device comprises a retractable shaft; a shaft biasing spring; and an actuator button. The retractable shaft is biased away from the actuator button by the shaft biasing spring. A magnetic attracting force is created between the retractable shaft and the actuator button upon actuation of the actuator button. Before actuation, a distance between the actuator button and the retractable shaft is great enough that the magnetic attracting force is less than a biasing force of the shaft biasing spring such that the retractable shaft is biased away from the actuator button. Upon actuation, the actuator button is depressed to make the distance between the actuator button and the retractable shaft sufficiently small such that the magnetic attracting force is greater than the biasing force of the shaft biasing spring to allow the retractable shaft to be biased towards the actuator button.

The actuator button may comprise a button return spring that biases the actuator button away from the retractable shaft. The device may further comprise a first magnet on the retractable shaft and a second magnet on the actuator button, the first magnet and the second magnet being of opposite polarities to create the magnetic attracting force. The device may further comprise a first magnet on one of the retractable shaft and the actuator button and a ferromagnetic material on the other of the retractable shaft and the actuator button. The device may further comprise a housing in which the retractable shaft and the actuator button are slidably arranged. The retractable shaft may comprise a collar positioned thereon, and the housing may comprise a shoulder positioned therein, and the shaft biasing spring may be compressibly positioned between the collar and the shoulder. The retractable shaft may include a medical tool.

In another example, a device comprises a retractable shaft and an actuator button. A first end of the retractable shaft includes a first magnet having a polarity and a first end of the actuator button includes a second magnet having the same polarity as the first magnet such that the first end of the retractable shaft is repelled from the first end of the actuator button. When the actuator button is pressed the first end of the actuator button travels past the first end of the retractable shaft such that the first magnet and the second magnet drive the retractable shaft towards the actuator button.

The device may further comprise a housing in which the retractable shaft and the actuator button are slidably arranged. The actuator button may comprise a button return spring positioned in the housing, the button return spring being configured to bias the actuator button away from the retractable shaft. The first end of the actuator button may comprise a plunger on which the second magnet is one of coupled to or integral with the plunger having a cavity for receiving the first magnet. Upon receiving the first magnet in a mouth portion of the cavity, the retractable shaft may be repelled farther into the cavity. Upon the retractable shaft being repelled farther into the cavity, an attractive force between the second magnet and a distal portion of the retractable shaft may draw the distal portion of the retractable shaft to the second magnet. Upon the retractable shaft being repelled farther into the cavity, an attractive force between the first magnet and a bottom of the cavity may draw the first magnet to the bottom of the cavity. The retractable shaft may include a medical tool.

In another example, a method comprises providing a housing; providing a shaft having a medical tool located thereon, the shaft being slidably positioned in the housing and biased to extend from a distal end of the housing; providing an actuator button slidably positioned in the housing, the actuator button extending from a proximal end of the housing; and providing a magnetic attracting force between the shaft and the actuator button upon actuation of the actuator button. Before actuation, a distance between the actuator button and the shaft is great enough that the magnetic attracting force is less than a biasing force acting on the shaft such that the shaft is biased away from the actuator button. Upon actuation, the actuator button is depressed to make the distance between the actuator button and the shaft sufficiently small such that the magnetic attracting force is greater than the biasing force acting on the shaft to allow the shaft to be biased towards the actuator button.

The method may further comprise providing a button return spring cooperably associated with the actuator button to bias the actuator button away from the shaft. The method may further comprise providing a first magnet on the shaft and a second magnet on the actuator button, the first magnet and the second magnet being of opposite polarities to create the magnetic attracting force.

In another example, a method comprises maneuvering a medical device to contact a tissue surface of a patient, the medical device having a shaft biased to extend from a distal end of a housing and further having an actuator button disposed at a proximal end of the housing, the shaft further having a medical tool associated therewith for contacting the tissue surface of the patient; and actuating the actuator button to retract the shaft into the housing.

In another example, a medical device comprises a housing having a distal end and a proximal end; a retractable shaft slidably located in the housing so as to extend from the distal end; and an actuator magnetically couplable to the retractable shaft and slidably located in the housing so as to extend from the proximal end. Upon actuation, the actuator is depressed to allow the retractable shaft to be magnetically biased towards the actuator and retracted into the housing.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications, and variances which fall within the scope of the appended claims.

We claim:

1. A device, comprising:
a retractable shaft including a medical tool, the medical tool configured for contacting a tissue surface of a patient;
a shaft biasing spring; and
an actuator button;
wherein the retractable shaft is biased away from the actuator button by the shaft biasing spring;
wherein a magnetic attracting force is created between the retractable shaft and the actuator button upon actuation of the actuator button;
wherein before actuation, a distance between the actuator button and the retractable shaft is great enough that the magnetic attracting force is less than a biasing force of the shaft biasing spring such that the retractable shaft is biased away from the actuator button; and
wherein upon actuation, the actuator button is depressed to make the distance between the actuator button and the retractable shaft sufficiently small such that the magnetic attracting force is greater than the biasing force of the shaft biasing spring to allow the retractable shaft to be biased towards the actuator button.

2. The device of claim 1, wherein the actuator button comprises a button return spring that biases the actuator button away from the retractable shaft.

3. The device of claim 1, further comprising a first magnet on the retractable shaft and a second magnet on the actuator button, the first magnet and the second magnet being of opposite polarities to create the magnetic attracting force.

4. The device of claim 1, further comprising a first magnet on one of the retractable shaft and the actuator button and a ferromagnetic material on the other of the retractable shaft and the actuator button.

5. The device of claim 1, further comprising a housing in which the retractable shaft and the actuator button are slidably arranged.

6. The device of claim 5, wherein the retractable shaft comprises a collar positioned thereon, and wherein the housing comprises a shoulder positioned therein, and wherein the shaft biasing spring is compressibly positioned between the collar and the shoulder.

7. A device, comprising:
a retractable shaft;
a shaft biasing spring; and
an actuator button;
further comprising a housing in which the retractable shaft and the actuator button are slidably arranged;
wherein the retractable shaft is biased away from the actuator button by the shaft biasing spring;
wherein a magnetic attracting force is created between the retractable shaft and the actuator button upon actuation of the actuator button;
wherein before actuation, a distance between the actuator button and the retractable shaft is great enough that the magnetic attracting force is less than a biasing force of the shaft biasing spring such that the retractable shaft is biased away from the actuator button; and
wherein upon actuation, the actuator button is depressed to make the distance between the actuator button and the retractable shaft sufficiently small such that the magnetic attracting force is greater than the biasing force of the shaft biasing spring to allow the retractable shaft to be biased towards the actuator button.

8. The device of claim 7, wherein the actuator button comprises a button return spring that biases the actuator button away from the retractable shaft.

9. The device of claim 7, further comprising a first magnet on the retractable shaft and a second magnet on the actuator button, the first magnet and the second magnet being of opposite polarities to create the magnetic attracting force.

10. The device of claim 7, further comprising a first magnet on one of the retractable shaft and the actuator button and a ferromagnetic material on the other of the retractable shaft and the actuator button.

11. The device of claim 7, wherein the retractable shaft comprises a collar positioned thereon, and wherein the housing comprises a shoulder positioned therein, and wherein the shaft biasing spring is compressibly positioned between the collar and the shoulder.

12. The device of claim 7, wherein the retractable shaft includes a medical tool.

13. A device, comprising:
a retractable shaft; and
an actuator button;
wherein a first end of the retractable shaft includes a first magnet having a polarity and a first end of the actuator button includes a second magnet having the same polarity as the first magnet such that the first end of the retractable shaft is repelled from the first end of the actuator button;
wherein when the actuator button is pressed the first end of the actuator button travels past the first end of the retractable shaft such that the first magnet and the second magnet drive the retractable shaft towards the actuator button; and
wherein the first end of the actuator button comprises a plunger on which the second magnet is one of coupled to or integral with the plunger having a cavity for receiving the first magnet.

14. The device of claim 13, further comprising a housing in which the retractable shaft and the actuator button are slidably arranged.

15. The device of claim 14, wherein the actuator button comprises a button return spring positioned in the housing, the button return spring being configured to bias the actuator button away from the retractable shaft.

16. The device of claim 13, wherein upon receiving the first magnet in a mouth portion of the cavity, the retractable shaft is repelled farther into the cavity.

17. The device of claim 16, wherein upon the retractable shaft being repelled farther into the cavity, an attractive force between the second magnet and a distal portion of the retractable shaft draws the distal portion of the retractable shaft to the second magnet.

18. The device of claim 16, wherein upon the retractable shaft being repelled farther into the cavity, an attractive force between the first magnet and a bottom of the cavity draws the first magnet to the bottom of the cavity.

19. The device of claim 13, wherein the retractable shaft includes a medical tool.

\* \* \* \* \*